Figure 1:
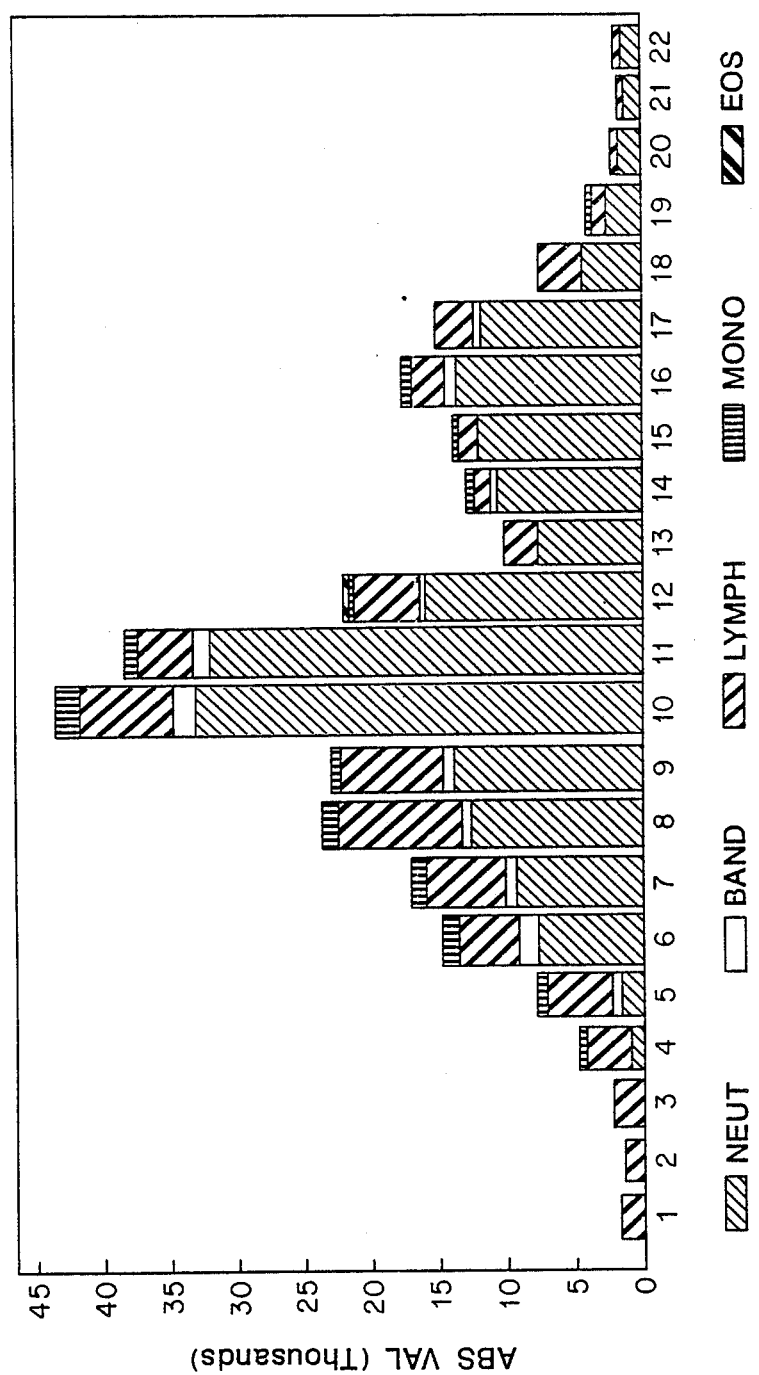

United States Patent [19]

Donahue

[11] Patent Number: 4,921,837
[45] Date of Patent: May 1, 1990

[54] TREATMENT OF AIDS-TYPE DISEASE

[75] Inventor: Robert E. Donahue, Littleton, Mass.

[73] Assignee: Genetics Institute Inc., Cambridge, Mass.

[21] Appl. No.: 81,489

[22] PCT Filed: Nov. 25, 1986

[86] PCT. No.: PCT/US86/02575

§ 371 Date: Jul. 24, 1987

§ 102(e) Date: Jul. 24, 1987

[87] PCT Pub. No.: WO87/03204

PCT Pub. Date: June 4, 1987

Related U.S. Application Data

[63] Continuation-in-part of Ser. No. 802,553, Nov. 27, 1985, abandoned.

[51] Int. Cl.⁵ ............................................. A61K 37/02
[52] U.S. Cl. .......................................... 514/2; 514/8; 514/44; 514/50; 514/885
[58] Field of Search .................... 435/68; 514/8, 2, 44, 514/885, 50; 530/351; 424/99

[56] References Cited

U.S. PATENT DOCUMENTS 4,230,697 10/1980 Nishida et al. ......................... 514/8

FOREIGN PATENT DOCUMENTS 2501692 9/1982 France ................................. 424/99
WO86/04587 8/1986 PCT Int'l Appl. .
2016477 8/1982 United Kingdom .

OTHER PUBLICATIONS

Mitsuya et al, cited in Chem. Abstracts, vol. 103:189277e, 1985.
Rook et al, J. Immunol., vol. 134, No. 3, 1985.
Kern et al, cited in Biol. Abstracts, vol. 79(11), No. 100547, 1985.
Motoyoshi et al, cited in Chem. Abstracts, vol. 99:1046a, 1982.
Metcalf et al, cited in Chem. Abstracts, vol. 91:49943e, 1979.
Spivak et al, cited in Biol. Abstracts, vol. 78(12), No. 92073, 1984.
Umemura, et al., *Clinical Research* 36(3): 570A (Abstract).
McDonagh, et al., *Clinical Research* 36(3):414A (Abstract).
Donahue, et al., Nature 321:872-875 (Jun. 1986).
Metcalf, et al, *Exp Hematol.* 15:1-9 (1987).
Tomonaga, et al., Blood 67:31-36 (Jan. 1986).
Emerson, et al., *J. Clin. Invest.* 76:1286-1290 (Sep. 1985).
Donahue, et al., Blood 66:1479-1481 (Dec. 1985).
Sieff, et al., Science 230:1171-1173 (Dec. 1985).
Donahue, et al., Nature 326:200-203 (Mar. 1987).
Yarchoan, et al., The Lancet, Mar. 15, 1986, pp. 575-580.
Sommadossi, et al., *Antimicrobial Agents and Chemotherapy,* 31:452-454 (Mar. 1987).
Johnson, et al., *British Journal of Hematology* 70:137-141 (1988).
Yarchoan, et al., *Scientific American* 259:110-119 (Oct. 1988).
Dagani, *Chemical & Engineering News,* Jun. 29, 1987, pp. 25-27.
"GM-CSF, Potential Therapy, May Assist AIDS Virus in Some Cases, Group Reports," *Wall Street Journal,* Sep. 23, 1988, p. 24.
Koyonagi, et al., Science 241:1673-1675, Sep. 1988.
Groopman, et al, N. Eng. J. Med. 317:593-598, Sep. 1987.
Perno, et al., "Replication of Human Immunodeficiency Virus in Monocytes," *The Journal of Experimental Medicine* 169:933-951, Mar. 1989.
"Companies Push Development of More Lymphokines" *Genetic Technology News* (Dec. 1984) p. 5.
"GM-CSF to be Used in AIDS Therapy" *Applied Genetic News* 7:7-8, (1986).
*Cetus Corporation Annual Report 1985* (Sep. 1985).

Primary Examiner—Jacqueline M. Stone
Attorney, Agent, or Firm—Bruce M. Eisen; Brian P. O'Shaughnessy; Luann Cserr

[57] ABSTRACT

Disclosed herein is the treatment of patients suffering from AIDS-type disease with a colony stimulating factor alone or together with erythropoietin, and/or an anti-viral agent and/or IL-2.

1 Claim, 2 Drawing Sheets

TREATMENT OF AIDS-TYPE DISEASE

This application is a continuation-in-part of U.S. Ser. No. 802,553, filed Nov. 27, 1985 now abandoned.

Acquired Immune Deficiency Syndrome, commonly known as AIDS, is a generally lethal disease of increasing notoriety. A less malignant form called AIDS-Related Complex (referred to as ARC) is also increasing in prevalence. For purposes of this invention these and related maladies may be hereinafter referred to generically as AIDS-type disease.

AIDS-type disease affects humans and other primates and is characterized by a general loss of the host immune response to invading pathogens. Another characteristic is pancytopenia, i.e. a marked depression in the hematological profile of the host. The etiologic agent is believed to be viral, and more specifically, retroviruses of the HTLV/LAV-type, now known as the human immunodeficiency virus (HIV). Related viruses with similar pathogenicity are found in monkeys and other simians. Despite various reports of successful treatments with diverse agents, there is still much need for effective therapy of AIDS-type disease.

According to my invention one or more primate colony stimulating factors are used to treat patients suffering from AIDS-type disease. The beneficial effects of this treatment can be measured by improved hematological profile (e.g. the reduction of cytopenia) and restoration of immune function.

Colony stimulating factors (CSFs) are a recognized class of proteins whose natural counterparts are produced in very low concentrations in the body. They stimulate the growth and development of various bone marrow progenitor cells into mature cells such as granulocytes, macrophages, megakaryocytes, erythrocytes, lymphocytes and mast cells. They obtain their name from the in vitro assay which measures the stimulation of colony formation by bone marrow cells plated in semi-solid culture media. These factors induce the formation of such colonies. Stated another way, CSFs are factors required for survival, proliferation and differentiation of the myeloid, lymphoid and erythroid progenitors.

A leading and preferred example of such a colony stimulating factor for use in this invention is GM-CSF, also known as granulocyte-macrophage colony stimulating factor It is described in detail in Wong et al Science Vol. 228, pp, 810–815 (May 17, 1985) and references cited therein. Wong et al. also teach its production via recombinant DNA techniques. While GM-CSF had been recognized as exhibiting significant in vitro activity on the various hematopoietic progenitor cells, its use in treatment of clinical conditions has been conjectural.

Another example of such colony stimulating factor is primate G-CSF, also known as beta-CSF or granulocyte-CSF. This factor produces colonies which contain primarily granulocytes and has been recently cloned. See Nagata et al., Nature, 319:415–418 (1986) and Souza et al. Science, 232:61–65, (1986).

Another colony stimulating factor for use in the treatment of this invention is primate IL-3, also known as pluripotent or multi-CSF. This CSF acts in an earlier stage in hematopoiesis. It has been described in Yang et al., Cell, 42:3–10, (1986).

Still another CSF within the scope of this invention is M-CSF, also known as CSF-1 or CSF-69. It produces colonies which contain primarily macrophages. It has been described in Kawasaki et al., Science, 230:291–296 (1985) and publications by E. R. Stanley. Its production by recombinant DNA techniques is described in U.S application Ser. No. 860,377. A truncated version is described in PCT/US86/00238.

Yet a further example of a CSF of this invention is CSF-309. This CSF acts in the early stages of hematopoiesis. It is described in U.S. CIP application Ser. No. 885,905 and Hirano et al, Nature, 324:73–76 (Nov. 6, 1986).

The CSFs can be systemically administered either intravenously or subcutaneously. One preferred form is via a subcutaneous implant, e.g., an osmotic continuous infusion pump. Numerous said implants are known in the art. The dosage regimen will be determined by the attending physician considering the condition of the patient, the severity of any infection and other clinical factors. Generally, the regimen as a continuous infusion should be in the range of 1–500 units per kilogram of body weight per minute. A preferred dose is in the range of 5 to 50 units per kilogram of body weight per minute. Progress can be monitored by periodic assessment of the hematological profile, e.g. hematocrit, CBC, reticulocyte count, platelet count and the like.

In another aspect of this invention, a primate patient having a depressed hematological profile is treated by co-administering effective amounts of a primate CSF and primate erythropoietin. The relative amount of erythropoietin should be within the range of 1–100 units per kilogram of body weight per minute. I contemplate that these two materials act synergistically to reduce both pancytopenia and anemia.

Erythropoietin is a natural protein factor which increases the differentiation and proliferation of erythrocytes. Human erythropoietin, along with its method of production via recombinant DNA techniques, is described in Jacobs et.al., Nature, Vol. 313, pp. 806–810 (Feb. 28, 1985) and references cited therein.

In a further embodiment of this invention, an immuno-comprised primate patient is treated by co-administering a primate CSF and primate IL-2. The relative amount of IL-2 should be within the range of 50–500 unit per kilogram of body weight per minute. I contemplate that these two materials will synergistically act to improve the patient's immune status. The relative ratios reflect the normal therapeutic amounts of each protein given separately. In a still further embodiment, erythropoietin is also co-administered in the above described amount with the CSF and IL-2 to further aid the immuno-compromised patient who is pancytopenic or anemic.

In another embodiment of the invention the CSF is co-administered with an anti-viral agent to a primate patient suffering from AIDS. A preferred anti-viral agent for use in conjunction with this invention is 3'-azido-3'deoxythymidine commonly referred to as AZT. A highly preferred combination is GM-CSF with AZT. The amount of AZT in this co-administration can be greater than the amount when AZT is the sole administered agent, thus permitting a higher therapeutic ratio.

The relative ratios and total amounts of CSF, antiviral agent, erythropoietin and/or IL-2 will be determined by the attending physician considering the condition of the patient, his hematological profile, the severity of any infection and other clinical factors. When systemically administered, the proteins for use in this invention are in the form of a pyrogen-free, parenterally acceptable aqueous solution. The preparation of such parenterally acceptable protein solutions, having due regard to pH, isotonicity, stability and the like, are within the skill of the art.

The following illustrate treatments according to this invention utilizing GM-CSF.

EXAMPLE 1

Figure 2:
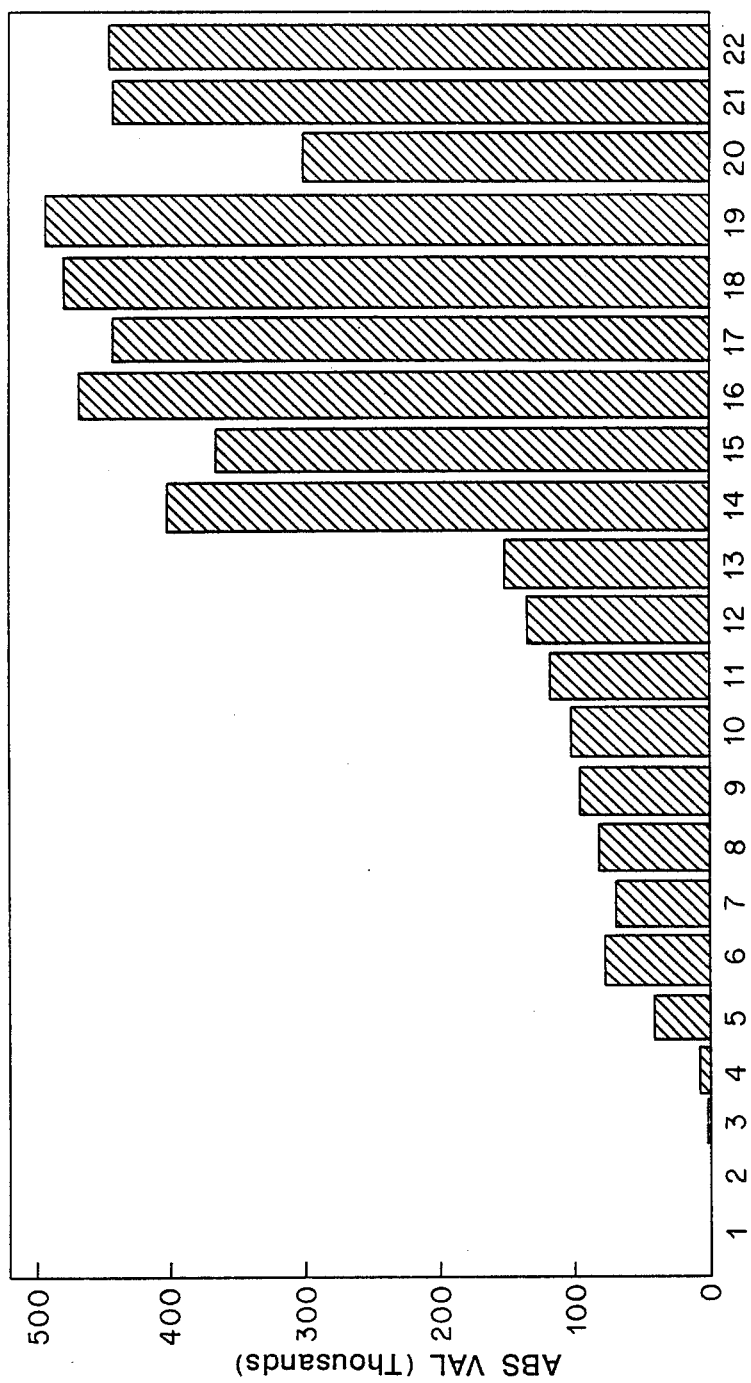

The patient was a severely debilitated, pancytopenic rhesus monkey naturally infected with the type D retrovirus (an AIDS-type disease). This animal received an aqueous solution of highly purified, pyrogen free recombinant human GM-CSF prepared as described in Wong et. al, supra. It was subcutaneously administered by means of a continuous osmotic infusion pump (Model 2ML1 produced by Alza Corporation, Palo Alto, Calif.) at a rate of 500 units per kilogram of body weight per minute for a period of seven days The patient's hematological progress is charted in FIG. 1. After an initial lag of three days the monkey's WBC began to rise significantly. From an initial leukocyte count of 1600 $\mu$l (98% lymphocytes, 2% monocytes) the white blood cell count was elevated to 23,900 on day 8 (52% polys, 2% bands, 42% lymphocytes, and 4% monocytes). Upon termination of the treatment on day 8 the white blood cell count peaked at 43,700 on day 10 and then began to decline returning to 1900 by day 19. FIG. 2 monitors the reticulocyte count, an important barometer of the patient's erythroid response.

The reticulocyte count revealed a dramatic increase upon infusion with this protein. This subsequently led to a significant increase in red blood cell count.

This illustrates the significant improvement in hematological profile obtainable by systemically treating a patient suffering an AIDS-type disease with a CSF.

EXAMPLE 2

The patient was a 35 year old human male having Kaposi's sarcoma and diagnosed as having AIDS in accordance with the criteria established by the U.S. Center for Disease Control. In a controlled study at the New England Deaconess Hospital, Boston, Mass., he was continuously infused intravenously with recombinant human GM-CSF having a specific activity of about $4 \times 10^6$ units/mg. at the rate of 3 units per kilogram of body weight per minute. This patient responded favorably to the infusion as measured by the white blood cell count increasing from 2,800 four days prior to the start of the study to 14,900 after receiving the aforesaid infusion for two weeks. The increase in total peripheral white blood cell count included absolute increases in neutrophils, banded neutrophils, and eosinophils. The patient expressed a subjective feeling of betterment and evinced a reduction in the size of Kaposi's sarcoma. Upon termination of the infusion two days later, the white blood cell count decreased to 4,000. While receiving the infusion the patient demonstrated no adverse effects to the administration of the protein.

EXAMPLE 3

In another 39 year old male AIDS patient who received a dose of 1 $\mu$g/kg per day of recombinant human GM-CSF as a continuous infusion, similar results were observed. This patient also responded favorably to the infusion, with an increase in the total white blood cell count of from 2,200 on the day of admission to 9,900 two weeks after the start of therapy. The increase in total peripheral white blood cell count included absolute increases in all subtypes of such cells including lymphocytes.

Other CSF's such as M-CSF, IL-3, G-CSF, and CSF-309 can be substituted for GM-CSF for an analogous treatment to that described above. Similarly, analogs or so-called second generation CSFs may be analogously employed.

What is claimed is:

1. In the method of treating a patient suffering from AIDS or ARC by administering 3'-azido-3'-deoxy-thymidine, the improvement to obtain a higher therapeutic ratio comprising co-administering an effective amount of GM-CSF to said patient.

* * * * *